US00PP13770P29

(12) United States Plant Patent
Kolster

(10) Patent No.: US PP13,770 P2
(45) Date of Patent: May 6, 2003

(54) BACCHARIS PLANT NAMED 'KOLMSIL'

(75) Inventor: Peter R. Kolster, Boskoop (NL)

(73) Assignee: Gebr. Kolster BV, Boskoop (NL)

( * ) Notice: Subject to any disclaimer, the term of this patent is extended or adjusted under 35 U.S.C. 154(b) by 0 days.

(21) Appl. No.: 10/158,956

(22) Filed: May 31, 2002

(51) Int. Cl.[7] ..... A01H 5/00
(52) U.S. Cl. ..... Plt./226
(58) Field of Search ..... Plt./226

(56) References Cited

U.S. PATENT DOCUMENTS

PP11,240 P * 2/2000 Gass ..... Plt./226

OTHER PUBLICATIONS

UPOV ROM GTITM Computer Database, GTI JOUVE retrieval software 2002/02, citations(s) for 'Kolmsil'.*

* cited by examiner

*Primary Examiner*—Bruce R. Campell
*Assistant Examiner*—W C Haas
(74) *Attorney, Agent, or Firm*—C. A. Whealy

(57) ABSTRACT

A new and distinct cultivar of Baccharis plant named 'Kolmsil', characterized by its upright and outwardly spreading plant habit; freely branching growth habit; freely flowering habit; and discoid inflorescences.

1 Drawing Sheet

BOTANICAL CLASSIFICATION/CULTIVAR DESIGNATION

*Baccharis halimifolia* cultivar Kolmsil.

BACKGROUND OF THE INVENTION

The present Invention relates to a new and distinct cultivar of Baccharis plant, botanically known as *Baccharis halimifolia*, and hereinafter referred to by the name 'Kolmsil'.

The new Baccharis was discovered as a cross-pollination of two unidentified selections of *Baccharis halimifolia*, not patented. The new Baccharis was discovered and selected by the Inventor in 1998 as a single flowering plant in a controlled environment in Boskoop, The Netherlands, within a population of the progeny resulting from the cross-pollination.

Asexual reproduction of the new Baccharis by cuttings was first conducted in Boskoop, The Netherlands in 1998. Since then, asexual reproduction by cuttings has shown that the unique features of this new Baccharis are stable and reproduced true to type in successive generations.

SUMMARY OF THE INVENTION

The cultivar Kolmsil has not been observed under all possible environmental conditions. The phenotype may vary somewhat with variations in environment such as temperature and light intensity without, however, any variance in genotype.

The following traits have been repeatedly observed and are determined to be the unique characteristics of 'Kolmsil'. These characteristics in combination distinguish 'Kolmsil' as a new and distinct Baccharis:

1. Upright and outwardly spreading plant habit.
2. Freely branching growth habit.

3. Freely flowering habit.
4. Discoid inflorescences.

Plants of the new Baccharis differ primarily from plants of the parent selections and other known selections and cultivars of Baccharis in plant size, leaf size, foliage coloration, time to flower, and inflorescence coloration.

BRIEF DESCRIPTION OF THE PHOTOGRAPHS

The accompanying colored photographs illustrate the overall appearance of the new Baccharis showing the colors as true as it is reasonably possible to obtain in colored reproductions of this type. Colors in the photographs may differ from the color values cited in the detailed botanical description which accurately describe the colors of the new Baccharis.

The photograph at the top of the sheet comprises a side perspective view of a typical flowering plants of 'Kolmsil' grown in an outdoor nursery.

The photograph at the bottom of the sheet is a close-up view of a typical inflorescence of 'Kolmsil'.

DETAILED BOTANICAL DESCRIPTION

The aforementioned photographs and following observations and measurements describe plants grown in Boskoop, The Netherlands, in an outdoor nursery under full sun conditions. The photographs and the observations and measurements were taken in October, 2001; plants were about three years old. During the summer, day temperatures ranged from 14 to 27° C. and night temperatures ranged from 7 to 14° C. Color references are made to The Royal Horticultural Society Colour Chart, 1995 edition, except where general terms of ordinary dictionary significance are used.

Botanical classification: *Baccharis halimifolia* cultivar Kolmsil.

Parentage:

*Female, or seed, parent.*—Unidentified selection of *Baccharis halimifolia*, not patented.

*Male, or pollen, parent.*—Unidentified selection of *Baccharis halimifolia*, not patented.

Propagation:

*Type.*—By cuttings.

*Time to initiate roots.*—About 30 days at 20° C.

*Time to produce a rooted plant.*—About 90 days at 18° C.

*Root description.*—Medium in thickness; moderate branching.

Plant description:

*Appearance.*—Perennial herbaceous shrub. Upright and outwardly spreading plant habit; broad inverted triangle. Very freely branching; about seven basal branches with about 16 lateral branches develop per plant; dense and full plants. Moderately vigorous growth habit.

*Plant height.*—About 170 cm.

*Plant width or area of spread.*—About 160 cm.

*Lateral branches.*—Length: About 25 cm. Diameter: About 3 mm. Internode length: About 1.5 cm. Strength: Moderately strong. Texture: Slightly rough; glabrous. Color, immature: 144B to 144C to close to 145A. Color, mature: 199B to 199C.

*Foliage description.*—Arrangement: Alternate; single. Length: About 5.6 cm. Width: About 3.5 cm. Shape: Elliptic to broadly oblanceolate. Apex: Acute. Base: Attenuate. Margin: Towards base, entire; towards apex, dentate. Venation pattern: Pinnate. Texture, upper and lower surfaces: Rough; glabrous. Color: Young and fully expanded foliage, upper surface: 137A to slightly darker than 137A. Young and fully expanded foliage, lower surface: 137B. Venation, upper and lower surfaces: 138B to 138C. Petiole: Length: About 2 cm. Diameter: About 1 mm. Texture, upper and lower surfaces: Glabrous. Color, upper and lower surfaces: 143C.

Inflorescence description:

*Appearance.*—Inflorescences held mostly above and beyond the foliage arranged in panicles. Inflorescences discoid, i.e., without ray florets. Inflorescences not persistent. Inflorescences face outward to upright.

*Flowering response.*—Plants flower continuous and freely from early October to mid-October in Boskoop, The Netherlands.

*Postproduction longevity.*—Inflorescences maintain good color and substance for about five days on the plant when grown in an outdoor environment. As a cut flowering stem, inflorescences maintain good color and substance for about ten days in an interior environment.

*Quantity of inflorescences.*—Freely flowering; about 300 open inflorescences and buds per lateral stem per flowering season.

*Fragrance.*—Faint; musky.

*Inflorescence bud.*—Length: About 4 mm. Diameter: About 0.4 mm. Shape: Ovoid. Color: 157A.

*Inflorescence size.*—Length: About 7 mm. Diameter: About 3 mm.

*Ray florets.*—None observed.

*Disc florets.*—Shape: Tubular, elongated. Apex: Acute. Length: About 6 mm. Diameter: About 0.5 mm. Number of disc florets per inflorescence: About 30. Color, immature and mature: 157A.

*Pappus.*—Appearance/arrangement: About 25 silky hairs per floret surrounding the style. Length: About 4.5 mm. Diameter: Less than 0.1 mm. Texture: Smooth. Color: 157D to 155C.

*Phyllaries.*—Length: About 2 mm. Diameter: About 1 mm. Shape: Narrowly ovate. Apex: Acute. Base: Fused. Margin: Entire. Texture: Smooth. Number of whorls per inflorescence: About four. Color, upper and lower surfaces: 143C; towards apex, 174A to 187D.

*Pedicels.*—Length: About 7 cm. Diameter: About 1 mm. Angle: About 30 to 45° from vertical. Strength: Strong. Texture: Smooth. Color: 143C.

*Reproductive organs.*—Androecium: None observed. Gynoecium: Pistils per floret: One. Pistil length: About 5 mm. Style length: About 4.5 mm. Style color: 157A. Stigma shape: Cleft, reflexed. Stigma color: Close to 182B to 182C. Ovary color: 155C.

*Fruit.*—Quantity per inflorescence: About 25. Type: Achene. Length: About 8 mm. Diameter: About 1 mm. Color: 157B to 157D.

*Seed.*—Quantity per fruit: One. Length: About 0.9 mm. Diameter: About 0.4 mm. Color: 157B.

Disease/pest resistance: Resistance to pathogens and pests common to Baccharis has not been observed on plants grown under outdoor conditions.

Temperature tolerance: Plants of the new Baccharis have been observed to tolerate temperatures from about −20 to 35° C.

It is claimed:

1. A new and distinct cultivar of Baccharis plant named 'Kolmsil', as illustrated and described.

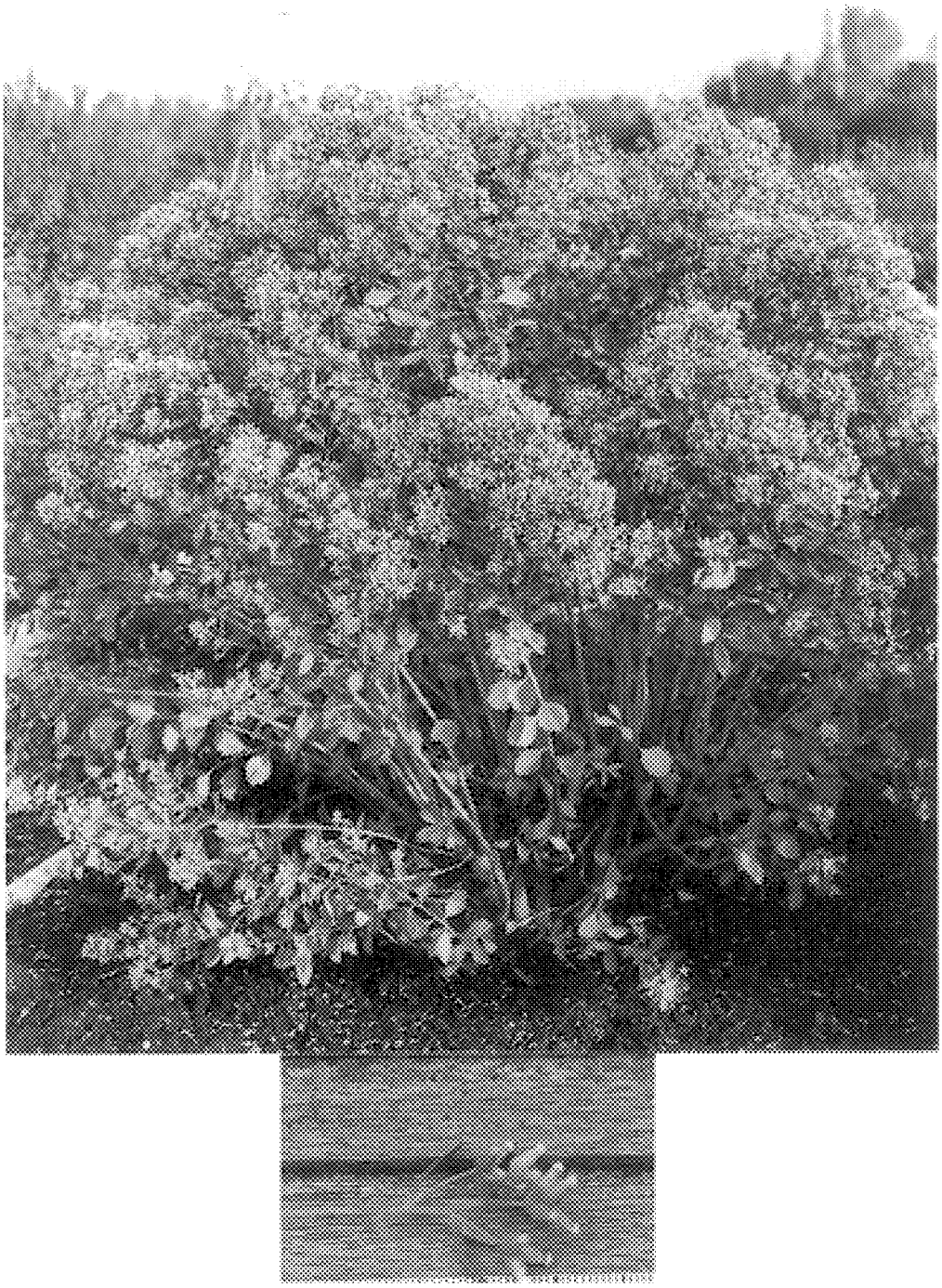

* * * * *